US012582835B2

(12) United States Patent
Fortkort et al.

(10) Patent No.: US 12,582,835 B2
(45) **Date of Patent: *Mar. 24, 2026**

(54) LIGHT THERAPY TREATMENT MODALITY WITH OSCILLATING AND NONOSCILLATING WAVELENGTHS

(71) Applicant: Reversal Solutions, Inc., Belmont, CA (US)

(72) Inventors: John A. Fortkort, Austin, TX (US); Annelise E. Barron, Redwood City, CA (US)

(73) Assignee: Reversal Solutions, Inc., Belmont, CA (US)

(*) Notice: Subject to any disclaimer, the term of this patent is extended or adjusted under 35 U.S.C. 154(b) by 384 days.

This patent is subject to a terminal disclaimer.

(21) Appl. No.: 17/893,104

(22) Filed: Aug. 22, 2022

(65) Prior Publication Data

US 2023/0055346 A1 Feb. 23, 2023

Related U.S. Application Data

(60) Provisional application No. 63/235,692, filed on Aug. 21, 2021.

(51) Int. Cl.
*A61N 5/06* (2006.01)
*A61N 5/073* (2006.01)

(52) U.S. Cl.
CPC .... *A61N 5/0622* (2013.01); *A61N 2005/0647* (2013.01); *A61N 2005/0652* (2013.01);
(Continued)

(58) Field of Classification Search
CPC .... A61N 2005/0626; A61N 2005/0633; A61N 2005/0643; A61N 2005/0647; A61N 2005/0652; A61N 2005/0659; A61N 2005/0662; A61N 2005/0663; A61N 5/0622; A61N 5/06–2005/073
(Continued)

(56) References Cited

U.S. PATENT DOCUMENTS 8,900,283 B2 12/2014 Johnson et al.
9,968,799 B2 5/2018 Johnson et al.
(Continued)

FOREIGN PATENT DOCUMENTS

KR 20210053631 A * 5/2021 ............. A61B 5/378
WO 2019173847 A1 9/2019

OTHER PUBLICATIONS

Hamblin M.R. Shining light on the head: Photobiomodulation for brain disorders. BBA Clin. 2016;6:113-124. Published Oct. 1, 2016. doi:10.1016/j.bbacli.2016.09.002.
(Continued)

*Primary Examiner* — Benjamin J Klein
*Assistant Examiner* — Vynn V Huh
(74) *Attorney, Agent, or Firm* — John A. Fortkort; Fortkort & Houston PC

(57) ABSTRACT

A method is provided for performing electromagnetic radiation therapy on a subject. The method comprises providing a device which emits electromagnetic radiation, wherein the electromagnetic radiation includes a first portion that oscillates between at least first and second distinct states, and a second non-oscillatory portion; and illuminating the subject with the electromagnetic radiation.

16 Claims, 5 Drawing Sheets

(52) U.S. Cl.
CPC ................. *A61N 2005/0659* (2013.01); *A61N 2005/0663* (2013.01); *A61N 2005/073* (2013.01)

(58) Field of Classification Search
USPC ..................................................... 607/88–94
See application file for complete search history.

(56) References Cited

U.S. PATENT DOCUMENTS

| | | | |
|---|---|---|---|
| 10,293,177 B2 | 5/2019 | Malchano et al. | |
| 10,391,330 B2 | 8/2019 | Bourke, Jr. et al. | |
| 10,478,635 B1 | 11/2019 | Nelson et al. | |
| 2014/0303547 A1 | 10/2014 | Loupis et al. | |
| 2017/0099713 A1* | 4/2017 | Perez ................... | H05B 47/115 |
| 2017/0304584 A1 | 10/2017 | Tsai et al. | |
| 2019/0314641 A1 | 10/2019 | Malchano et al. | |

OTHER PUBLICATIONS

Zein R., Selting W., Hamblin M.R. Review of light parameters and photobiomodulation efficacy: dive into complexity. J Biomed Opt. Dec. 2018;23(12):1-17. doi: 10.1117/1.JBO.23.12.120901. PMID: 30550048.

Hipskin S.G., Grover F.L. Jr, Fort T.R., Helffenstein D., Burke T.J., Quint S.A.,Bussiere G., Stone M., Hurtado T. Pulsed Transcranial Red/Near-Infrared Light Therapy Using Light-Emitting Diodes Improves Cerebral Blood Flow and Cognitive Function in Veterans with Chronic Traumatic Brain Injury: A Case Series. Photomed Laser Surg. Nov. 28, 2018. doi: 10.1089/pho.2018.4489. Epub ahead of print. PMID: 30418082.

Purushothuman, S., Johnstone, D. M., Nandasena, C., Mitrofanis, J., & Stone, J. (2014). Photobiomodulation with near infrared light mitigates Alzheimer's disease-related pathology in cerebral cortex—evidence from two transgenic mouse models. Alzheimers Res Ther. 2014;6(1):2. Published Jan. 3, 2014. doi:10.1186/alzrt232.

Hamblin M.R. Photobiomodulation for traumatic brain injury and stroke. J Neurosci Res. Apr. 2018;96(4):731-743. doi: 10.1002/jnr. 24190. Epub Nov. 13, 2017. Erratum in: J Neurosci Res. Mar. 2019;97(3):373. PMID: 29131369; PMCID: PMC5803455.

Alais D., Locke S.M., Leung J., Van Der Burg E. No attentional capture from invisible flicker. Sci Rep. Jul. 5, 2016;6:29296. doi: 10.1038/srep29296. PMID: 27377759; PMCID: PMC4932510.

Martorell A.J., Paulson A.L., Suk H.J., Abdurrob F., Drummond G.T., Guan W., Young J.Z., Kim D.N., Kritskiy O., Barker S.J., Mangena V., Prince S.M., Brown E.N., Chung K., Boyden E.S., Singer A.C., Tsai L.H. Multi-sensory Gamma Stimulation Ameliorates Alzheimer's-Associated Pathology and Improves Cognition. Cell. Apr. 4, 2019;177(2):256-271.e22. doi: 10.1016/j.cell.2019.02. 014. Epub Mar. 14, 2019. PMID: 30879788; PMCID: PMC6774262.

Spiegler A., Knösche T.R., Schwab K., Haueisen J., Atay F.M. Modeling brain resonance phenomena using a neural mass model. PLoS Comput Biol. Dec. 2011;7(12):e1002298. doi: 10.1371/journal. pcbi.1002298. Epub Dec. 22, 2011. PMID: 22215992; PMCID: PMC3245303.

Köster, M., Martens, U., Gruber, T. 2017. Memory entrainment by visually evoked theta-gamma coupling. doi:10.1101/191189.

Ferreira, A.C., Castellano, J.M., 2019. Leaving the Lights on Using Gamma Entrainment to Protect against Neurodegeneration. Neuron 102, 901-902.. doi:10.1016/j.neuron.2019.05.020.

Poil, S.-S., De Haan, W., Van Der Flier, W.M., Mansvelder, H.D., Scheltens, P., Linkenkaer-Hansen, K., 2013. Integrative EEG biomarkers predict progression to Alzheimer's disease at the MCI stage. Frontiers in Aging Neuroscience 5.. doi:10.3389/fnagi.2013.00058.

Bredesen D.E. Inhalational Alzheimer's disease: an unrecognized—and treatable—epidemic. Aging (Albany NY). Feb. 2016;8(2):304-13. doi: 10.18632/aging.100896. PMID: 26870879; PMCID: PMC4789584.

Zaccara I.M., Jardine A.P., Mestieri L.B., Quintana R.M., Jesus L., Moreira M.S., Grecca F.S., Martins M.D., Poli Kopper P.M. Influence of photobiomodulation therapy on root development of rat molars with open apex and pulp necrosis. Braz Oral Res. Aug. 26, 2019;33:e084. doi: 10.1590/1807-3107bor-2019.vol33.0084. PMID: 31460610.

Herrmann, C.S., 2001. Human EEG responses to 1?100?Hz flicker: resonance phenomena in visual cortex and their potential correlation to cognitive phenomena. Experimental Brain Research 137, 346-353.. doi: 10.1007/s002210100682.

Herrmann C.S., Demiralp T. Human EEG gamma oscillations in neuropsychiatric disorders. Clin Neurophysiol. Dec. 2005;116(12):2719-33. doi: 10.1016/j.clinph.2005.07.007. Epub Oct. 25, 2005. PMID: 16253555.

Stefánsson, J.F. (2018). Gamma wave inducing effects of 40 Hz flickering light in humans.

Garza, K.M., Zhang, L., Borron, B., Wood, L.B., Singer, A.C., 2020. Gamma Visual Stimulation Induces a Neuroimmune Signaling Profile Distinct from Acute Neuroinflammation. The Journal of Neuroscience 40, 1211-1225.. doi:10.1523/jneurosci.1511-19.2019.

Iaccarino, H.F., Singer, A.C., Martorell, A.J., Rudenko, A., Gao, F., Gillingham, T.Z., Mathys, H., Seo, J., Kritskiy, O., Abdurrob, F., Adaikkan, C., Canter, R.G., Rueda, R., Brown, E.N., Boyden, E.S., Tsai, L.-H., 2016. Gamma frequency entrainment attenuates amyloid load and modifies microglia. Nature 540, 230-235.. doi:10.1038/nature20587.

Bauer F, Cheadle SW, Parton A, Müller HJ, Usher M. Gamma flicker triggers attentional selection without awareness. Proc Natl Acad Sci U S A. Feb. 3, 2009;106(5):1666-71. doi: 10.1073/pnas. 0810496106. Epub Jan. 5, 2009. PMID: 19124766; PMCID: PMC2635817.

Adaikkan C., Middleton S.J., Marco A., Pao P.C., Mathys H., Kim D.N., Gao F., Young J.Z., Suk H.J., Boyden E.S., McHugh T.J., Tsai L.H. Gamma Entrainment Binds Higher-Order Brain Regions and Offers Neuroprotection. Neuron. Jun. 5, 2019;102(5):929-943.e8. doi: 10.1016/j.neuron.2019.04.011. Epub May 7, 2019. PMID: 31076275; PMCID: PMC6697125.

DreamSpa Distributor Guide (2019).

Carolyn Weaver, "Brain-wave treatment for Alzheimer's is promising, but the first human subject is left behind", Salon (Dec. 13, 2017).

Tani, Y., Fujiwara, T., Kondo, K., 2020. Association Between Adverse Childhood Experiences and Dementia in Older Japanese Adults. JAMA Network Open 3, e1920740.. doi:10.1001/jamanetworkopen.2019.20740.

Williams, J., Ramaswamy, D., Oulhaj, A., 2006. None. BMC Neuroscience 7, 21.. doi:10.1186/1471-2202-7-21.

* cited by examiner (a) delta band (below 4Hz)

(b) theta band (4–8 Hz)

(c) alpha band (8–13Hz)

(d) mu-rhythm (8–12Hz)

(e) beta band (13–30Hz)

(f) gamma band (30–50Hz)

LIGHT THERAPY TREATMENT MODALITY WITH OSCILLATING AND NONOSCILLATING WAVELENGTHS

CROSS-REFERENCE TO RELATED APPLICATION

This application claims the benefit of priority of U.S. provisional application No. 63/235,692, filed Aug. 21, 2021, having the same inventor and the same title, and which is incorporated herein by reference in its entirety.

FIELD OF THE DISCLOSURE

The present application relates generally to light therapy, and more specifically to light therapy using a light source which emits a first oscillating wavelength and a second non-oscillating wavelength.

BACKGROUND OF THE DISCLOSURE

Within the last couple of decades, a significant amount of research has focused on the use of antimicrobial peptides in the treatment of multi-drug resistant bacteria. Natural antimicrobial peptides (AMPs) are known to defend a wide array of organisms against bacterial invaders. These AMPs have shown potential as supplements for (or replacements of) conventional antibiotics, since few bacteria have evolved resistance to them.

AMPs destroy bacteria in various ways. Some AMPs kill bacteria by permeating the cytoplasmic membrane and causing depolarization or leakage of internal cell materials. Other AMPs function by targeting anionic bacterial constituents, such as DNA, RNA, or cell wall components. Bacterial resistance to AMPs is rare, possibly because AMPs have evolved along with the resistance mechanisms that are designed to evade them. Moreover, the targets of many AMPs (such as bacterial plasma membranes and anionic intracellular macromolecules) are sufficiently general that changes to the sequence of the AMP can be made to subvert resistance, without having any significant adverse impact on overall functionality.

Although AMPs have been actively studied for decades, they have yet to achieve widespread clinical use. This is due, in part, to the vulnerability of many peptide therapeutics to rapid in vivo degradation, which dramatically reduces their bioavailability.

The foregoing problems have led to the development of peptidomimetics, which are small, protein-like chains designed to mimic a peptide. Peptidomimetics may be made by modifying an existing peptide, or may be based on similar systems that mimic peptides, such as peptoids and β-peptides.

Peptoids (poly-N-substituted glycines) are isomers of peptides in which side chains are attached to the backbone amide nitrogen rather than to the α-carbon. Antimicrobial peptoids have been described, for example, in U.S. Pat. No. 8,445,632 (Barron et al.), entitled "Selective Poly-N-Substituted Glycine Antibiotics", which is incorporated herein by reference in its entirety.

Peptoids are particularly well-suited for AMP mimicry. Peptoids are easily synthesized using conventional peptide synthesis equipment, and provide access to diverse sequences at relatively low cost. Submonomer synthetic methods are known that may be utilized to impart a wide variety of chemical functionalities to peptoids. Consequently, peptoids are highly and finely tunable. Furthermore, they are protease-resistant, and can be designed to form amphipathic helices that resist thermal and chaotropic denaturation.

Neurons in the human body use action potentials (APs) to transmit information. These brief and uniform pulses of electrical activity are generated when the membrane potential of a neuron reaches a threshold value. The resulting pulses travel down the axon toward synapses and terminate at postsynaptic neurons, where they initiate postsynaptic currents (PSCs). The PSCs then summate to either trigger or inhibit new APs. The resulting sequence or "train" of APs may contain information based on various coding schemes and may produce various results. In simple motor functions such as muscle flexure, the strength at which the function occurs may depend solely on the firing rate of neurons. Other functions may rely on more complex temporal codes that are a function of the precise timing of single APs. These complex temporal codes may be tied to external stimuli (for example, those generated by the auditory system) or may be generated intrinsically by neural circuitry.

The human brain contains a large number of neurons. The electrochemical activity of neurons in generating the electrical currents required for APs occurs in a synchronized manner that is characterized by macroscopic oscillations. These oscillations may be characterized by their frequency, amplitude and phase, and may be monitored and depicted graphically in an electroencephalogram (EEG). The graphical depiction of these macroscopic oscillations in an EEG are often referred to as "brainwaves".

Five common brainwave bandwidths (delta, theta, alpha, beta and gamma) have been identified in humans, each of which is associated with specific mental states. [Thompson, M., & Thompson, L. (2003). The neurofeedback book: An introduction to basic concepts in applied psychophysiology. Wheat Ridge, CO: The Association for Applied Psychophysiology and Biofeedback. Walter, V. J., & Walter, W. Grey]. Within these bandwidths, various sub-categories (high, low alpha and beta, and sensorimotor rhythm) have also been identified, which are associated with different mental activities.

By way of example, delta waves (0.5-3 Hz) are the dominant brainwaves observed during deep sleep. Theta waves (4-7 Hz) are typically associated with drowsy or relaxed states. Low alpha waves (8-10 Hz) are frequently associated with meditative states and inward thinking (daydreams, dissociation from external stimulation). High alpha waves (11-12 Hz) are associated with creativity and the alert but calm state needed for peak performance. Sensorimotor rhythms (13-15 Hz), which are frequently categorized as low beta, are believed to occur predominantly in the still state before a reactive psychomotor action. Low beta waves (16-20 Hz) are associated with intellectual activity and problem-solving. High beta waves (21-37 Hz) are found in emotional and anxious states; and gamma waves (38-42 Hz) are associated with attention and intense cognitive activity. [Id.] An excess of brainwave activity in any of the foregoing bandwidths or sub-categories may also be associated with a particular state or condition. Thus, for example, excessive beta and gamma activity has been associated with hyperaroused states, such as those occurring during stress, anxiety, or insomnia. [Perlis, M. L., Merica, H., Smith, M. T. & Giles, D. E. (2001). Beta EEG activity and insomnia. Sleep Medicine Reviews, 5(5), 363-374].

Brainwave entrainment (sometimes referred to as brainwave synchronization or neural entrainment) may be utilized to modulate the brainwaves in a subject to induce, for example, a particular mental state in the subject. Brainwave entrainment typically involves the manipulation of the frequency of brainwaves (or the associated patterns of firing of neural synapses) by suitable rhythmic or periodic external stimuli, which may include auditory, visual, or tactile stimuli. The effectiveness of brain entrainment is believed to result from the tendency of the brain to naturally synchronize its brainwave frequencies with the oscillations of periodic external stimuli. Since (as noted above) particular patterns of neural firing have been associated with certain mental states, it is believed that brainwave entrainment may be utilized to induce desired states of consciousness by modulating brainwaves in a subject. Such states of consciousness may be those which are conducive, for example, to studying, sleeping, exercising, meditating, or doing creative work.

Early work in brainwave entrainment focused on the use of visual stimuli. However, Chatrian et al. found that brainwave entrainment could also be achieved with auditory stimuli alone (specifically, clicking sounds). [Chatrian, E. G., Peterson, M. C., & Lazarte, J. A. (1960). Responses to clicks from the human brain: Some depth electrograph observation. Electroencephalography and Clinical Neurophysiology, 12, 479-489]. This led to the discovery by Oster that binaural beats (which are produced by the simultaneous application of first and second distinct, single frequency sine wave tones to first and second ears of a subject) stimulate brain activity that corresponds to the rhythm of the difference in the two stimuli frequencies. [Oster, G. (1973). Auditory beats in the brain. Scientific American, 229, 94-102].

It has since been found that the foregoing modes of brainwave entrainment (namely, visual and auditory entrainment) may be combined. This technique, which is the subject of U.S. Pat. No. 3,838,417 (Charas), is referred to variously as "audio visual stimulation" (AVS), "light and sound stimulation," "audio photic stimulation," or "audio visual entrainment." AVS has been utilized in various clinical applications involving attention deficit disorder (ADD), academic performance, cognition, depression, stress management, tension, pain, PTSD, migraine headaches, hypertension, and stroke.

AVS brainwave entrainment may be open-loop or closed-loop. In closed-loop AVS brainwave entrainment, the subject is attached to EEG recording electrodes. Brain activity is measured through these electrodes and is used by the AVS device to provide light and sound stimulation based on the properties of the brain activity recorded. Hence, the stimulation is driven by the subject's brainwaves, and thus provides real-time feedback based on the activity of the user. This approach is termed "neurofeedback" and is typically conducted with the assistance of a clinician.

Open-loop AVS brainwave entrainment is not dependent on the subject's brainwave activity. In this approach, entrainment occurs in response to flickering light and audio tones of particular frequencies. Unlike the closed-loop approach, this form of AVS entrains brain activity in response to the designated frequencies (which are typically selected to induce a desired mental state), without any brain activity feedback provided to the AVS device. Various consumer products have been developed to implement open-looped AVS brainwave entrainment. These include, for example, the brainwave entrainment device sold under the trademark EquiSync®.

Other types of light therapy in particular have also been developed in the art that do not necessarily involve brainwave entrainment. For example, photobiomodulation therapy (PBMT) is a type of light therapy that utilizes non-ionizing electromagnetic energy to trigger photochemical changes in cellular structures that are receptive to photons. Various devices have been developed in the art to implement PBMT or processes related thereto. Examples of such devices are described, for example, in U.S. 2019/0246463A1 (Williams et al.)., U.S. US2019/0175936 (Gretz et al.), WO2019/053625 (Lim), U.S. U.S. 2014/0243933 (Ginggen), U.S. 2019/0142636 (Tedford et al.), U.S. Pat. No. 7,354,432 (Eells et al.), U.S. 2008/0091249 (Wang), U.S. Pat. No. 10,391,330 (Bourke et al.) and U.S. 2016/0129278 (Mayer). Various salutary effects have been ascribed to PBMT including, for example, promotion of tissue healing or regeneration, reduction in inflammation, and general analgesic effects.

BRIEF DESCRIPTION OF THE DRAWINGS

FIG. 5(a) depicts brainwaves from the delta band. FIG. 5(b) depicts brainwaves from the theta band. FIG. 5(c) depicts brainwaves from the alpha band. FIG. 5(d) depicts brainwaves from the mu-rhythm band. FIG. 5(e) depicts brainwaves from the beta band. FIG. 5(f) depicts brainwaves from the gamma band.

SUMMARY OF THE DISCLOSURE

Figure 1:
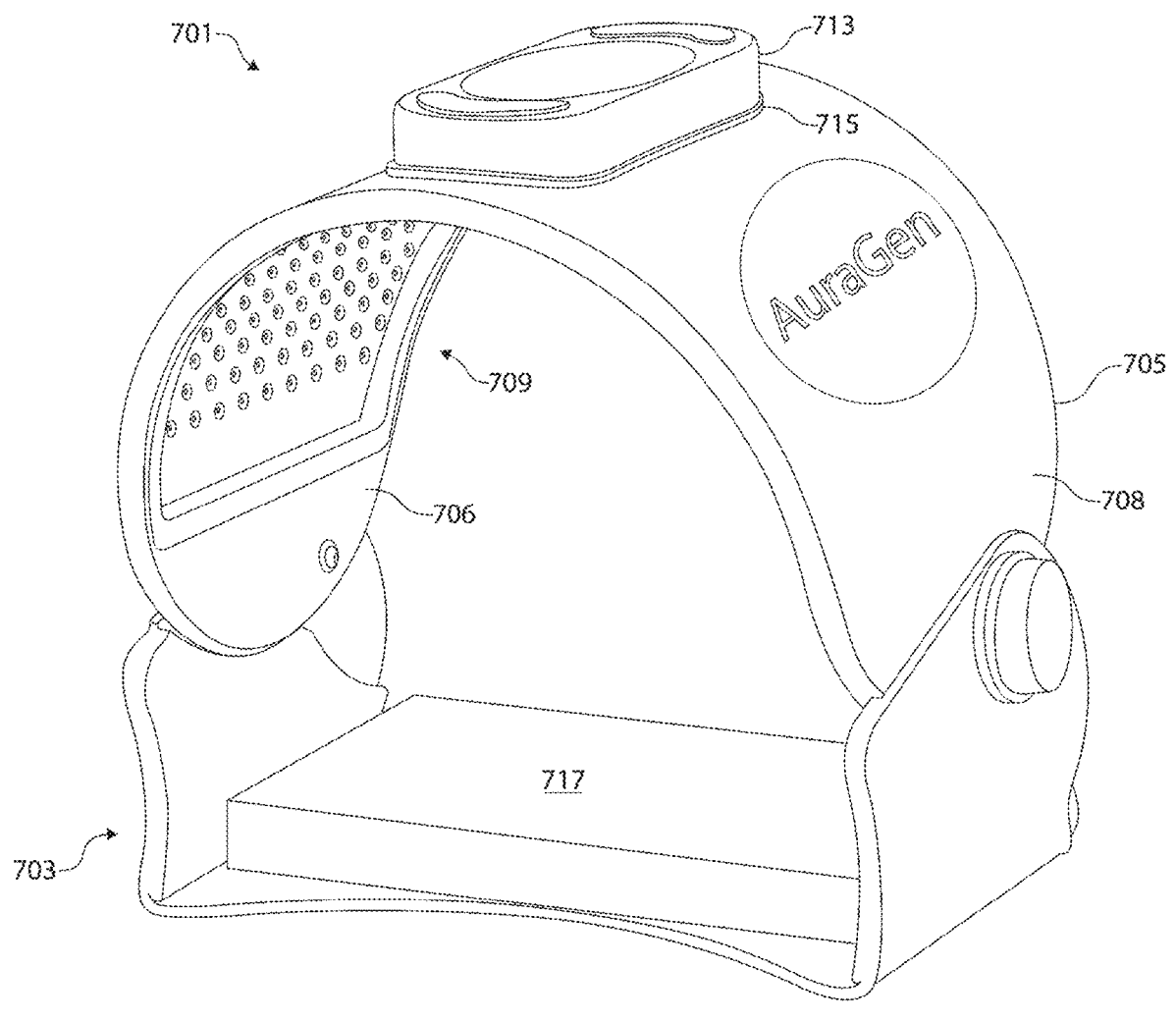
FIGS. 1-4 are illustrations of an embodiment of a device which may be utilized to implement the brainwave entrainment methodologies disclosed herein.
Figure 2:
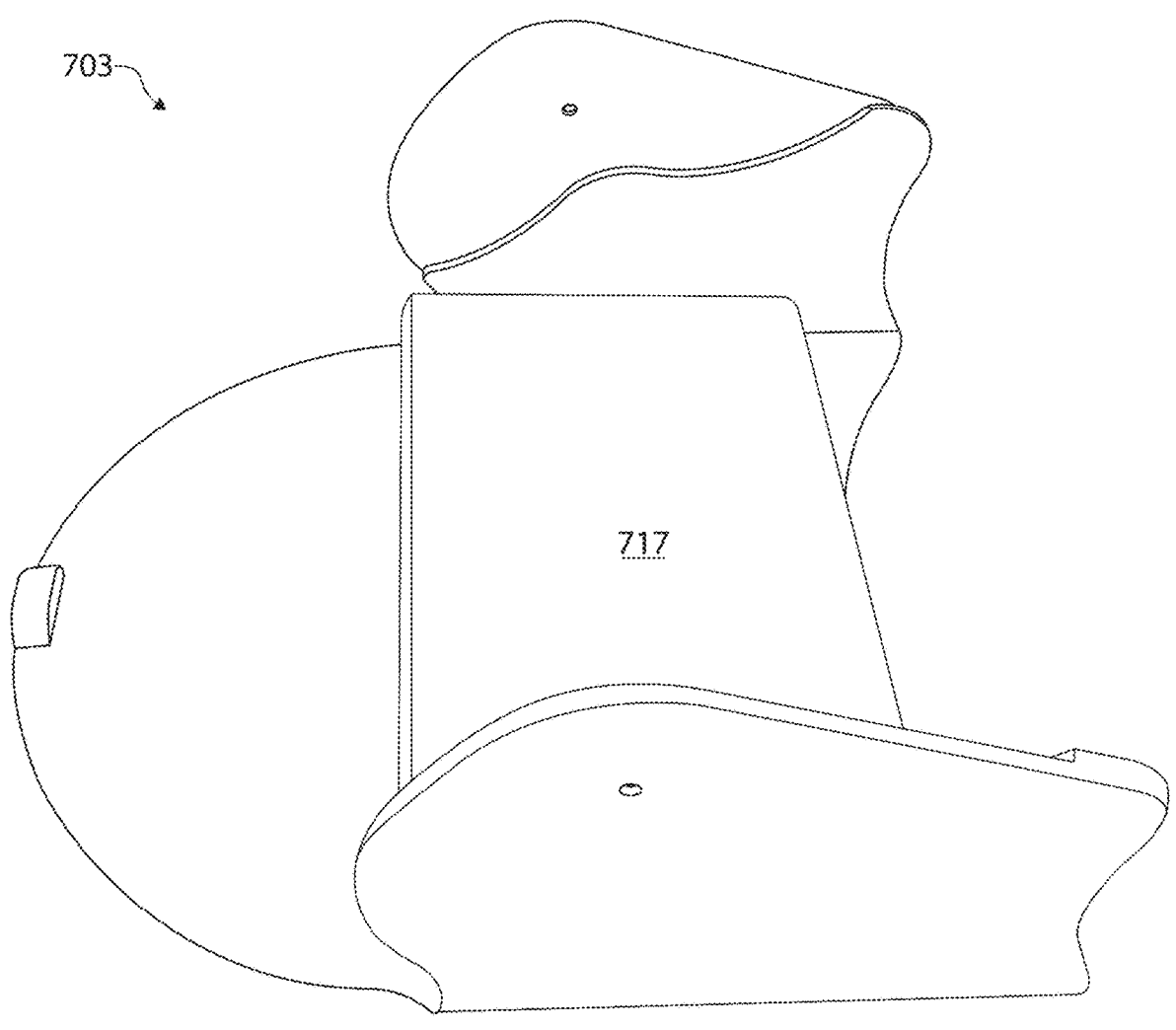

In one aspect, a method is provided for performing electromagnetic radiation therapy on a subject. The method comprises providing a device which emits electromagnetic radiation, wherein the electromagnetic radiation includes a first portion that oscillates between at least first and second distinct states, and a second non-oscillatory portion; and illuminating the subject with the electromagnetic radiation.

In another aspect, a light therapy device is provided which comprises an LED array; a first set of LEDs disposed in said LED array which emit electromagnetic radiation that oscillates between at least first and second distinct states; and a second set of LEDs disposed in said LED array which emit non-oscillating electromagnetic radiation.

In a further aspect, an LED array is provided which comprises a first set of LEDs which emit electromagnetic radiation in a first polarization state; a second set of LEDs which emit electromagnetic radiation in a second polarization state which is distinct from the first polarization state; a third set of LEDs which emit non-oscillating electromagnetic radiation; and an oscillator which oscillates electromagnetic radiation output by the LED array between at least said first and second polarization states.

In yet another aspect, a method is provided for performing electromagnetic radiation therapy on a subject. The method comprises providing an electromagnetic radiation fixture equipped with an LED array containing (a) a first set of LEDs which emit electromagnetic radiation in a first polarization state, (b) a second set of LEDs which emit electromagnetic radiation in a second polarization state, and (c) a third set of LEDs which emit non-oscillating electromagnetic radiation; positioning the electromagnetic radiation fixture such that electromagnetic radiation emitted by the fixture is directed at the subject and the subject is illuminated by the first, second and third set of LEDs; and oscillating the LED array between first and second illumination states selected from the group consisting of (a) a first illumination state in which the first set of LEDs are illuminated and the second set of LEDs are not illuminated, and a second illumination state in which the first set of LEDs are not illuminated and the second set of LEDs are illuminated, (b) a first illumination state in which the first set of LEDs are powered on and the second set of LEDs are powered off, and a second illumination state in which the first set of LEDs are powered off and the second set of LEDs are powered on, and (c) a first illumination state in which the power supply to the first set of LEDs is at a maximum and the power supplied to the second set of LEDs is at a minimum, and a second illumination state in which the power supply to the first set of LEDs is at a minimum and the power supply to the second set of LEDs is at a maximum.

DETAILED DESCRIPTION

While several devices and methodologies have been developed in the art to date for providing light therapy or open-loop brainwave entrainment, further improvement is needed in these devices and methodologies. In particular, existing light therapy devices and methodologies often require the user to elect between specific sets of benefits to be obtained. For example, the oscillating electromagnetic radiation typically used in brainwave entrainment and the non-oscillatory electromagnetic radiation sometimes used in light therapy each have been found to have unique advantages.

It has now been found that beneficial, and in some cases synergistic, effects may be obtained, especially in electromagnetic radiation therapy or light therapy applications (including, but not limited to, brainwave entrainment), by providing a device which emits electromagnetic radiation, wherein the electromagnetic radiation includes a first portion that oscillates between at least first and second distinct states, and a second non-oscillatory portion. The device may then be utilized to illuminate a subject with the electromagnetic radiation. This may be accomplished, for example, by equipping the device with an LED array having first and second groups of LEDs therein, wherein the first group of LEDs emits electromagnetic radiation that oscillates between the at least first and second distinct states, and wherein the second group of LEDs emits steady or non-oscillating electromagnetic radiation.

Without wishing to be bound by theory, it is believed that devices and methodologies of the type disclosed herein provide distinct benefits associated with both oscillatory and non-oscillatory electromagnetic radiation therapy. For example, it has been found that non-oscillatory electromagnetic radiation may be superior to oscillatory electromagnetic radiation in stimulating microglia and suppressing inflammation. On the other hand, the use of oscillating electromagnetic radiation provides the ability to perform brainwave entrainment.

Various types of oscillating radiation may be utilized in the devices and methodologies described herein. For example, such oscillation may occur in electromagnetic radiation between two or more polarization states. This may include, for example, oscillating electromagnetic radiation between nonpolarized and polarized states, oscillating electromagnetic radiation between distinct orientations of polarization (for example, oscillating electromagnetic radiation between right-handed and left-handed polarization states), oscillating electromagnetic radiation between types of polarization (for example, oscillating electromagnetic radiation between two or more of circularly polarized, elliptically polarized or linearly polarized states), or oscillating electromagnetic radiation between at least two distinct planes or polarization (for example, oscillating electromagnetic radiation between at least two polarization states in which the electromagnetic radiation has an electric field confined to first and second non-coplanar planes, respectively).

Various combinations of the foregoing may also be utilized. For example, embodiments are possible in which oscillation of electromagnetic radiation occurs between at least first and second states which differ in at least two parameters selected from the group consisting of polarized/nonpolarized, orientation of polarization, type of polarization, and plane of polarization.

The oscillation frequency between polarization states of electromagnetic radiation may be selected to achieve various results. For example, in light therapy applications, this oscillation frequency may be selected to entrain brainwaves in one or more of the five common brainwave bandwidths (delta, theta, alpha, beta and gamma). In these and other applications, the electromagnetic radiation or the periodicity thereof may be synchronized to sound waves or beats. These include, without limitation, binaural beats and sound having nested wave functions or nested frequencies of the type described in aforementioned U.S. Ser. No. 63/055,320 (Fortkort et al.).

Various devices may be utilized to implement the methodologies disclosed herein and using any of the waveforms described above. FIGS. 1-4 illustrate a particular, nonlimiting embodiment of such a device. The device 101 depicted therein comprises a base 103 (shown in isolation in FIG. 2) having a peripheral element 105 attached thereto and, optionally, an audio headset (not shown; the need for a headset may be determined, for example, by whether the methodology uses traveling waves originating from the same source, or standing waves generated by two distinct sources). The base 103 and peripheral element 105 define an opening 107 in which a user's head is placed (see FIG. 3). The base 103 and/or peripheral element 105 may be equipped with an audio jack, a Bluetooth transmitter, or other suitable provisions as necessary or desirable to support the use of an audio headset by the user.

The base 103 in this particular embodiment is equipped with a pillow 111 for user comfort, and to provide the user with the ability to lie down or sleep during a session. The peripheral element 105 has a first major inward-facing surface 106 and a second major outward-facing surface 108. The first major surface 106 is equipped with an LED array 109 which can be activated with a remote control 113 to illuminate the user's head at one or more wavelengths. The second major surface 108 is equipped with a holder 115 for the remote control 113. The remote control 113, which is shown in greater detail in FIG. 23, may also be utilized to modulate the light emitted by the LED array 109, to select one or more wavelengths of light emitted by the LED array 109, and to control the playback of one or more audio files or tracks.

Figure 3:
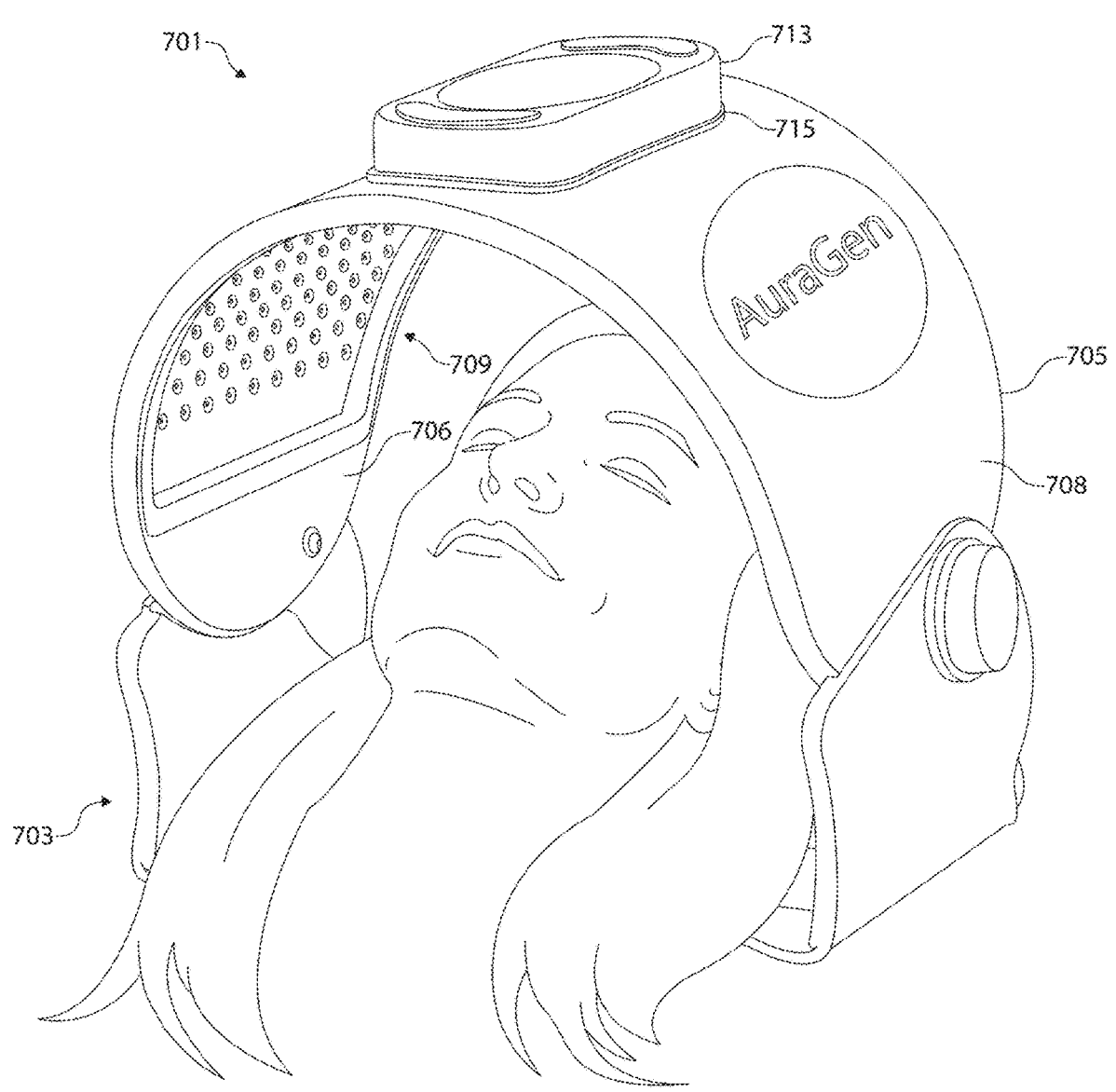
Figure 4:
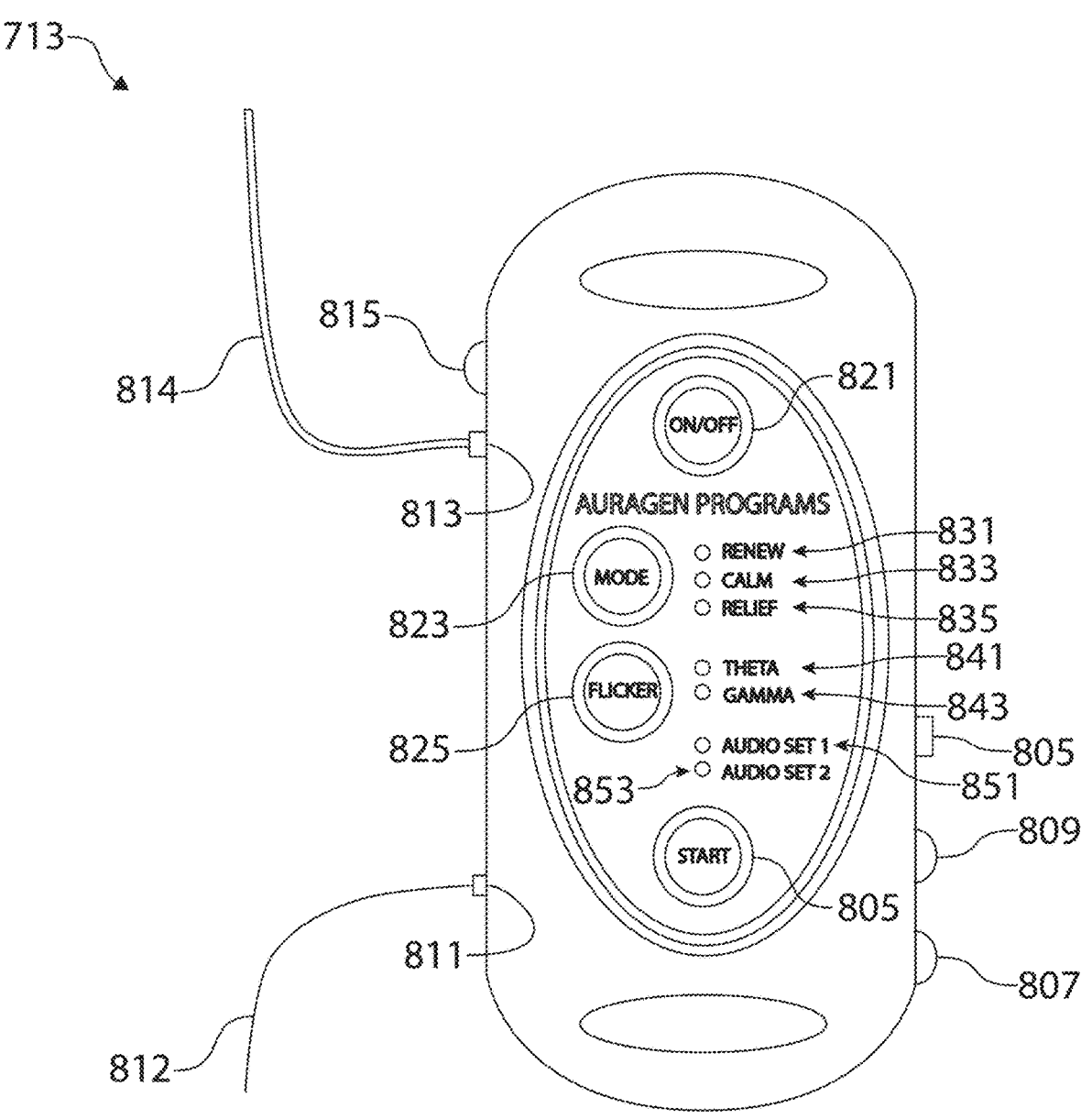

In use, a user's head is placed in the opening 107 such that the back of the user's head is on the pillow 111 and such that the user is facing the first major surface 106 of the peripheral portion 105 as shown in FIG. 3. The user (or possibly a clinician or other assistant) then uses the remote control 113 to activate the device 101 and to cause it to function in one or more selected modes. Regarding the latter, it is to be noted that the device 101 may be programmed with various algorithms which cause it to function in particular ways, some of which are described in greater detail below. The device 101 may also be programmed to play music or soundtracks, which may be advantageously matched to the particular algorithm being implemented by the device 101.

In some embodiments, the device may include a port to allow plugin of additional LED portable devices that may be place in the mouth of the user (via, for example, a mouth guard). In other embodiments, the device may include a small pad that may be wrapped or directly applied to a specific body part of the user. In still other embodiments, the device may include a set of googles or glasses that are placed over the eyes of the user to provide focused treatment to those areas, or to prevent treatment of those areas. Of course, it will be appreciated that any of the foregoing accessories may be utilized in combination in various embodiments of the systems and methodologies disclosed herein.

Various LEDs 109 or other light sources which emit at various wavelengths may be utilized in the devices and methodologies disclosed herein. However, the use of light sources which emit at wavelengths in the red, infra-red and blue-turquoise regions of the spectrum are preferred, and the use of light sources which emit at about 470 nm, 670 nm and 870 nm are especially preferred. In a preferred mode of operation, these light sources are made to oscillate or flicker in the theta or gamma band.

It will be appreciated that light may be emitted at the foregoing wavelengths in various manners, including sequentially or simultaneously. For example, the LED array 109 may be operated to emit electromagnetic radiation at a single wavelength (i.e., monochromatically) or at multiple wavelengths. In some cases, the LED array 109 may include a first set of LEDs that are operated to emit light at a first wavelength, a second set of LEDs that are operated to emit light at a second wavelength, and (optionally) a third set of LEDs that are operated to emit light at a third wavelength. In other cases, the LED array 109 may be operated such that all of the LEDs in the array emit light at a first wavelength for a first period of time, all of the LEDs in the array emit light at a second wavelength for a second period of time, and (optionally) all of the LEDs in the array emit light at a third wavelength for a third period of time.

The particular wavelength(s) of emission of the LED array 109, the duration of those emissions, the frequency of oscillation (if any), the intensity of the emitted light, the selection of accompanying audio tracks or files (if any), and/or the oscillation of any accompanying audio tracks, files or component(s) thereof, may be selected to achieve a desired physiological or psychological effect. It will be appreciated that, in some embodiments, the duration of emission for any particular wavelength of light may remain constant or may vary during the course of a therapy session. It will further be appreciated that, in some embodiments, any of the LEDs in the LED array 109 may be operated to emit two or more wavelengths of light, including broadband radiation or white light.

The devices and methodologies disclosed herein may be utilized as an effective tool in treating a subject for certain psychological or physiological conditions, or for prevention of these conditions. These conditions include, but are not limited to, traumatic brain injury, addiction or dependence (including, for example, addiction to, or dependence on, opioids, amphetamines, stimulants, alcohol or cannabis), depression (and more specifically, clinical depression or major depression), PTSD, developmental trauma disorder, traumatic brain injury and its sequelae, and Alzheimer's disease. In a preferred embodiment of the methodology disclosed herein, a subject is first diagnosed as suffering from one of the foregoing conditions, and then the device is utilized to treat the subject.

Various aspects of the systems and methodologies described herein have been described above with respect to the particular, non-limiting embodiments disclosed herein. It will be appreciated that these various aspects may be employed in various combinations (including various subcombinations) or permutations in accordance with the teachings herein.

For example, while the use of light sources which emit at wavelengths in the red, infra-red and blue-turquoise regions of the spectrum are preferred, and the use of light sources which emit at about 470 nm, 670 nm and 870 nm are especially preferred, it will be appreciated that the devices and methodologies disclosed herein may utilize various other frequencies or wavelengths of electromagnetic radiation to achieve desired physiological or psychological effects. These wavelengths or frequencies may be selected, for example, from the visible, infrared or ultraviolet regions of the electromagnetic spectrum.

Similarly, in a preferred mode of operation, the intensities of one or more of these light sources are made to oscillate or flicker in the theta or gamma frequency band during at least a portion of a therapy session. However, embodiments are possible in which the light sources are made to oscillate or flicker at other frequencies, or in which the light sources (or elements thereof) operate in a manner which is not time varying. Embodiments are also possible in which the light sources are made to oscillate or flicker at harmonics of the foregoing frequencies.

While the embodiment of FIGS. 1-4 is a preferred embodiment of the device described herein, it will be appreciated that devices of various shapes, configurations, layouts and functionalities may be utilized in the practice of the methodologies disclosed herein, and these light therapy units may be provided with various accessories.

For example, in some embodiments, devices may be utilized that are adapted to illuminate one or more inner surfaces of a subject's oral cavity. In such embodiments, a light therapy unit utilized for this purpose may be fashioned as a standalone device, while in other embodiments, such a light therapy unit may be fashioned as an accessory to a main light therapy unit which is utilized to illuminate the outer surfaces of a subject's head. In embodiments of the latter type, the accessory may be adapted to communicate with the main device such that the accessory is controlled by, or acts in concert with, the main device.

In some instances of embodiments of a device adapted to illuminate one or more inner surfaces of a subject's oral cavity, the light therapy unit may be equipped with a mouth guard which is in optical communication with a light source by way of a suitable light guide, and which distributes light received from the light source in a suitable manner. In some cases, the mouthguard may be customized to the user. By way of example but not limitation, such a mouth guard may be adapted to direct suitable wavelengths of light to various surfaces of the oral cavity of a subject, including the teeth, gums, upper or lower mouth, and throat. The mouth guard, light guide or portions thereof may be equipped with suitable materials that specularly or diffusely transmit or reflect incident radiation in one or more directions. In addition to their possible use in treating physiological or psychological conditions, these embodiments may offer additional benefits such as, for example, the treatment or prevention of gingivitis and other bacterial infections.

In some embodiments of the devices disclosed herein, measures may be taken to ensure that the device is applied to only specific parts of the user's body. For example, in some embodiments, the aforementioned light therapy unit which is adapted to illuminate one or more inner surfaces of a subject's oral cavity may be used by itself such that only these surfaces are exposed to the light therapy. Similarly, in some embodiments, the user may be equipped with glasses or goggles such that the user's eyes or optical nerves are not exposed to the therapeutic radiation, or such that this light is concentrated on the user's eyes or optical nerves. In still other embodiments, an optical pad or other suitable means may be utilized to apply the device only to the back of a user's neck, or to a user's chest (alone or in combination with the application of entraining frequencies to the user's head).

Preferred embodiments of the devices disclosed herein are adapted to allow the user to lie down or otherwise assume a state of repose during a light therapy session. Such embodiments may include, for example, a pillow or one or more deformable pads which support the user's head during light therapy. Here, it is notable that many other devices in the art which are designed for light therapy require the user to remain in a sitting or standing position for the duration of the therapy.

In some embodiments of the devices disclosed herein, the device may be equipped with a suitable controller, which may be wireless or wired. The controller may be programmable or pre-programmed, and may be equipped with suitable programming instructions (which may include an operating system) recorded in a tangible, non-transient medium that cause the light therapy device to operate in various modes or to perform various functions. These modes or functions may be selected or optimized for the treatment of various portions of a subject's body, or for the treatment of particular physiological or psychological conditions.

Various parameters (and ranges of these parameters) may be utilized in devices and methodologies disclosed herein. These include, without limitation, wavelength, frequency, entrainment waveform (if applicable), energy, fluence, power, irradiance, intensity, pulse mode, treatment duration, and repetition. These parameters and their values may be selected to treat a subject for certain psychological or physiological conditions, to lessening the severity or effects of these conditions, and/or to preventing the occurrence of these conditions. These conditions include, but are not limited to, traumatic brain injury, opioid addiction (including, for example, heroin addiction or addiction to prescription opioids), alcohol misuse disorder or alcohol dependence, nicotine dependence or addiction, depression (and more specifically, clinical depression or major depression), mild cognitive impairment, dementia, Alzheimer's disease, attention deficit disorder, developmental trauma disorder, and autism.

It will be appreciated that the devices disclosed herein, and the components thereof, may be equipped with suitable optical elements to achieve various purposes. Such optical elements (or portions thereof) may be diffusely or specularly reflective or transmissive. Suitable optical elements may include, but are not limited to, reflective elements, polarizers, color shifting elements, filters, light guides (including, without limitation, optical fibers, light pipes and waveguides), prismatic elements, lenses (including Fresnel lenses), and lens arrays.

Figure 5:
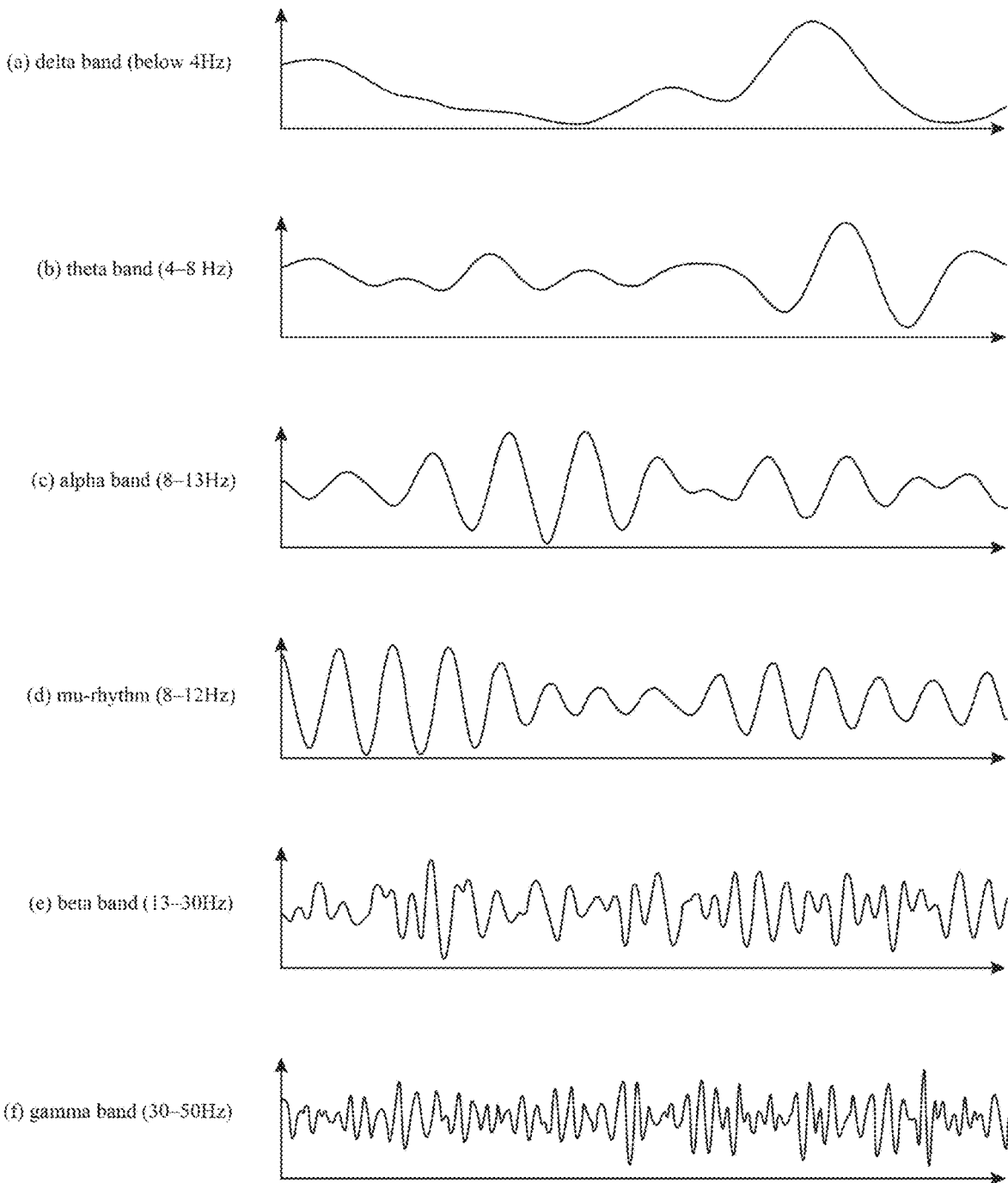
FIG. 5 is a graphical depiction of brainwaves from different frequency ranges.

In preferred embodiments of the systems and methodologies disclosed herein, one or more audio tracks or audio files may be provided that may be modulated, coordinated and/or synchronized with the plurality of LEDs or the light emitted therefrom. Preferably, the audio tracks or audio files include sound that is modulated, coordinated and/or synchronized with the LEDs or the light emitted therefrom at one or more frequencies selected from the ranges depicted in FIG. 5. The audio tracks or files (alone, or in combination with any light wavelengths utilized) may be selected to achieve a desired physiological or psychological effect in the user, either alone or in combination with the light therapy.

One skilled in the art will further appreciate that the systems and methodologies disclosed herein may be used not only to treat various physiological or psychological conditions, but to prevent them from occurring in the first place. For example, these systems and methodologies may be adapted to prophylactically prevent the onset of depression, PTSD, ADHD, opioid addiction (for example, heroine or oxycodone), or conditions resulting from traumatic brain injury, or of conditions which might otherwise result from the foregoing.

The systems and methodologies disclosed herein may be utilized in conjunction with other methodologies or techniques. For example, these systems and methodologies may be used in combination with emotional freedom technique (EFT) tapping. EFT tapping is a holistic healing technique that may be utilized to treat various issues including, without limitation, stress, anxiety, phobias, emotional disorders, chronic pain, addiction, weight control, and limiting beliefs. EFT tapping involves tapping with the fingertips on specific meridian endpoints of the body, while focusing on negative emotions or physical sensations. Proponents of the method claim that it calms the nervous system, rewires the brain to respond in healthier ways, and restores the body's balance of energy.

One skilled in the art will further appreciate that the optimal parameters for a light therapy session may depend on a variety of factors including, but not limited to, the condition being treated (or prevented), the physiological or psychological state of the user, the user's biometrics, and other such factors. In some use cases, selection of these parameters may be made by, or in coordination with, a physician, a psychiatrist, or other healthcare provider. These parameters may include, but are not limited to, the wavelengths of light to be utilized, the audio tracks or files to accompany the light therapy, the frequencies of oscillation utilized for the intensity in any of the wavelengths or light or sound, the portions of the user's head or body to be exposed to the light therapy, and the duration of the treatment.

While the devices and methodologies disclosed herein have frequently been described with reference to the use of traveling waves originating from a common source, one skilled in the art will appreciate that various embodiments of these methodologies and devices may also be produced which utilize waves originating from distinct sources (e.g., standing waves). In some embodiments, various devices, materials or other such measures may be taken to cause or prevent reflection of the waves used for light therapy.

The devices and methodologies disclosed herein have frequently been described or illustrated with respect to light therapy devices. However, it is to be understood that these devices and methodologies may have many uses in other fields and applications. These include, without limitation, their use in photic stimulation, including intermittent photic stimulation.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims. It will also be appreciated that the various features set forth in the claims may be presented in various combinations and sub-combinations in future claims without departing from the scope of the invention. In particular, the present disclosure expressly contemplates any such combination or sub-combination that is not known to the prior art, as if such combinations or sub-combinations were expressly written out.

What is claimed is:

1. A method for performing electromagnetic radiation therapy on a subject, comprising:

providing a device which emits electromagnetic radiation, wherein the electromagnetic radiation includes a first portion that oscillates between at least first and second distinct states at a frequency within the range of about 0.5 Hz to 50 Hz, wherein the first state is a first polarization state, and the second state is a second polarization state distinct from said first polarization state, and a second portion that does not oscillate within said range; and illuminating the subject with the electromagnetic radiation.

2. The method of claim 1, wherein the device has a higher luminous flux in the first state than in the second state for the first portion of electromagnetic radiation.

3. The method of claim 1, wherein the device has a luminous flux that is essentially constant for the second portion of electromagnetic radiation.

4. The method of claim 1, wherein the first and second polarization states are linearly polarized polarization states.

5. The method of claim 1, wherein the first and second polarization states are circularly polarized polarization states.

6. The method of claim 1, wherein the first and second polarization states are elliptically polarized polarization states.

7. The method of claim 1, wherein the electromagnetic radiation is linearly polarized in the first polarization state and has an electric field which is confined to a first plane that is orthogonal to the direction of propagation of the electromagnetic radiation in the first polarization state, wherein the electromagnetic radiation is linearly polarized in the second polarization state and has an electric field which is confined to a second plane that is orthogonal to the direction of propagation of the electromagnetic radiation in the second polarization state, and wherein the first and second planes are not coplanar.

8. The method of claim 1, wherein the electromagnetic radiation is circularly polarized in the first polarization state and has an electric field which is confined to a first plane that is orthogonal to the direction of propagation of the electromagnetic radiation in the first polarization state, wherein the electromagnetic radiation is circularly polarized in the second polarization state and has an electric field which is confined to a second plane that is orthogonal to the direction of propagation of the electromagnetic radiation in the second polarization state, and wherein the first and second planes are not coplanar.

9. The method of claim 1, wherein the electromagnetic radiation is elliptically polarized in the first polarization state and has an electric field which is confined to a first plane that is orthogonal to the direction of propagation of the electromagnetic radiation in the first polarization state, wherein the electromagnetic radiation is elliptically polarized in the second polarization state and has an electric field which is confined to a second plane that is orthogonal to the direction of propagation of the electromagnetic radiation in the second polarization state, and wherein the first and second planes are not coplanar.

10. The method of claim 1, wherein the electromagnetic radiation is linearly polarized in the first polarization state, and is circularly polarized in the second polarization state.

11. The method of claim 1, wherein the electromagnetic radiation is circularly polarized in the first polarization state, and is elliptically polarized in the second polarization state.

12. The method of claim 1, wherein the electromagnetic radiation is selected from the group consisting of (a) circularly polarized in a left-handed orientation in the first polarization state, and circularly polarized in a right-handed orientation in the second polarization state, (b) elliptically polarized in a left-handed orientation in the first polarization state, and elliptically polarized in a right-handed orientation in the second polarization state, (c) elliptically polarized in a left-handed orientation in the first polarization state, and is circularly polarized in a left-handed orientation in the second polarization state, and (d) linearly polarized in the first polarization state and has an electric field which is confined to a first plane that is orthogonal to the direction of propagation of the electromagnetic radiation in the first polarization state, wherein the electromagnetic radiation is circularly polarized in the second polarization state and has an electric field which is confined to a second plane that is orthogonal to the direction of propagation of the electromagnetic radiation in the second polarization state, and wherein the first and second planes are not coplanar.

13. The method of claim 1, wherein the electromagnetic radiation is circularly polarized in the first polarization state and has an electric field which is confined to a first plane that is orthogonal to the direction of propagation of the electromagnetic radiation in the first polarization state, wherein the electromagnetic radiation is elliptically polarized in the second polarization state and has an electric field which is confined to a second plane that is orthogonal to the direction of propagation of the electromagnetic radiation in the second polarization state, and wherein the first and second planes are not coplanar.

14. The method of claim 1, wherein the electromagnetic radiation is linearly polarized in the first polarization state and has an electric field which is confined to a first plane that is orthogonal to the direction of propagation of the electromagnetic radiation in the first polarization state, wherein the electromagnetic radiation is elliptically polarized in the second polarization state and has an electric field which is confined to a second plane that is orthogonal to the direction of propagation of the electromagnetic radiation in the second polarization state, and wherein the first and second planes are not coplanar.

15. The method of claim 1, wherein the first portion is emitted by a first set of LEDs, and wherein the second portion is emitted by a second set of LEDs.

16. The method of claim 15, wherein said first and second sets of LEDs are interspersed with each other in an LED array.

* * * * *